United States Patent
Kupferschmid et al.

(10) Patent No.: US 7,857,755 B2
(45) Date of Patent: Dec. 28, 2010

(54) MEDICAL INSTRUMENT FOR ENDOSCOPIC INTERVENTIONS

(75) Inventors: Markus Kupferschmid, Emmingen-Liptingen (DE); Christian Walter, Emmingen-Liptingen (DE)

(73) Assignee: Karl Storz GmbH & Co. KG (DE)

( * ) Notice: Subject to any disclaimer, the term of this patent is extended or adjusted under 35 U.S.C. 154(b) by 1064 days.

(21) Appl. No.: 11/441,409

(22) Filed: May 25, 2006

(65) Prior Publication Data

US 2006/0270904 A1 Nov. 30, 2006

(30) Foreign Application Priority Data

May 27, 2005 (DE) .................. 10 2005 024 352

(51) Int. Cl.
*A61B 1/00* (2006.01)
*A61B 1/12* (2006.01)

(52) U.S. Cl. .................. 600/131; 600/125; 600/136; 600/156

(58) Field of Classification Search .................. 600/108, 600/114, 123, 131, 136, 153, 156, 182, 158, 600/125, 154, 155
See application file for complete search history.

(56) References Cited

U.S. PATENT DOCUMENTS

| | | | | |
|---|---|---|---|---|
| 3,261,350 A | * | 7/1966 | Wallace | 600/182 |
| 3,383,192 A | * | 5/1968 | Siegmund | 65/410 |
| 4,517,962 A | * | 5/1985 | Heckele | 600/156 |
| 4,736,733 A | | 4/1988 | Adair | 128/6 |
| 4,762,120 A | | 8/1988 | Hussein | |
| 4,986,622 A | | 1/1991 | Martinez | 350/96.15 |
| 5,193,135 A | * | 3/1993 | Miyagi | 385/117 |
| 5,518,501 A | | 5/1996 | Oneda et al. | 600/127 |
| 5,621,830 A | | 4/1997 | Lucey et al. | 385/25 |
| 5,810,718 A | * | 9/1998 | Akiba et al. | 600/153 |
| 5,846,183 A | * | 12/1998 | Chilcoat | 600/136 |
| 6,387,044 B1 | * | 5/2002 | Tachibana et al. | 600/114 |
| 6,468,520 B1 | | 10/2002 | Rowe et al. | 424/78.08 |
| 6,494,826 B1 | * | 12/2002 | Chatenever et al. | 600/112 |
| 6,855,109 B2 | * | 2/2005 | Obata et al. | 600/158 |
| 2002/0082475 A1 | * | 6/2002 | Stahl et al. | 600/114 |
| 2002/0125857 A1 | | 9/2002 | Mastaler et al. | |
| 2005/0080342 A1 | | 4/2005 | Gilreath et al. | 600/476 |

FOREIGN PATENT DOCUMENTS

| DE | 19933015 A1 | 5/2000 |
|---|---|---|
| DE | 199 25 323 A1 | 12/2000 |
| EP | 1 325 704 | 7/2003 |

OTHER PUBLICATIONS

European Search Report, Sep. 7, 2006, 5 pages.

* cited by examiner

*Primary Examiner*—Linda C Dvorak
*Assistant Examiner*—Alireza Nia
(74) *Attorney, Agent, or Firm*—St. Onge Steward Johnston & Reens LLC

(57) ABSTRACT

The invention relates to a medical instrument for endoscopic interventions having a hollow shaft and a handle that supports the shaft, and in which the handle contains at least one channel that continues in the hollow shaft. To produce a medical instrument that can be flexibly inserted and in addition can be well cleaned it is proposed with the invention that the handle can be removably secured on the shaft by means of a coupling mechanism.

10 Claims, 2 Drawing Sheets

MEDICAL INSTRUMENT FOR ENDOSCOPIC INTERVENTIONS

FIELD OF THE INVENTION

The invention relates to a medical instrument for endoscopic interventions, having a hollow shaft and a handle that supports the shaft, and in which the handle contains at least one channel that continues in the hollow shaft.

BACKGROUND OF THE INVENTION

Endoscopic instruments with at least one channel configured in their handle are known in the art in various embodiments. In these state-of-the-art medical instruments, the shaft and the handle are inseparably joined together so that only one shaft can be used for gripping. In addition to this restricted applicability because of the fixed connection of shaft and handle, the state-of-the-art instruments have the disadvantage that the continuous channels are difficult to clean.

Consequently it is the aim of the invention to create a medical instrument for endoscopic interventions that can be applied flexibly and in addition is easy to clean.

SUMMARY OF THE INVENTION

This aim is fulfilled by the invention in a manner characterized in that the handle can be removably secured on the shaft by means of a coupling mechanism.

Because of the invention's separability of the shaft and handle, it is possible to secure various shafts on a single handle. Likewise, for instance, shafts can be provided with individually adapted handles. The ease of dismantling the medical instruments, in addition, facilitates the cleaning of instruments of this configuration.

According to a first practical embodiment, in which the at least one channel is configured as a light channel equipped with light-conducting fibers, it is proposed with the invention that a separate channel is installed in the hollow shaft for inserting the light-conducting fibers, and that the light-conducting fibers of the light channel on the handle side and of the light channel on the shaft side are ground and polished on the end surfaces that face one another. Such a light channel is necessary to conduct light into the examination site by way of the lens of an endoscopic instrument for observation and examination. Grinding and polishing of the light-conducting end surfaces that are to be coupled to one another, allows the greatest possible degree of unhindered transmission of light from the light channel on the handle side into the light channel on the shaft side.

Reflections that disturb luminous power can be avoided according to the invention through the fact that, with shaft and handle in coupled position, the mutually facing end surfaces of the fibers of the light channel on the handle side and of the light channel on the shaft side are oriented exactly centered on one another.

To minimize light losses caused by the residual small air gap between the mutually facing end surfaces of the fibers of the light channel on the handle side and of the light channel on the shaft side, it is proposed with the invention that in the area of the coupling spots between the light channel on the handle side and the light channel on the shaft side, an optically active substance, in particular an optical gel, is applied on the ends of the fibers.

Errors in centering the central orientation of the handle-side and shaft-side light-conducting fibers can further be compensated if the light-conducting cluster in a light channel has a greater diameter than the light-conducting cluster in the other light channel that is to be coupled with this light channel. The light-conducting fiber cluster here advantageously has the greater diameter in the handle-side light channel, first because more space is available in the handle than in the instrument shaft and secondly because the light-conductor on the light-source side is advantageously of greater diameter in order to ensure a complete illumination of the light conductor on the object side.

According to a second practical embodiment, in which the at least one channel is configured as a flushing and/or suction channel, it is proposed with the invention that in the area of the coupling spot between each channel on the handle side and the hollow shaft on the shaft and on the handle, a projecting part and a corresponding recess for inserting the projecting part are formed. The projecting parts and corresponding recesses in each other component, besides causing a continuation of the handle-side channel into the hollow shaft, result in a centering of the shaft and handle on one another, which facilitates the coupling of the two components.

To ensure that the shaft and the handle in the area of the coupling spot of the flushing and/or suction channel are connected pressure-tight with the hollow shaft, it is proposed with the invention that every projecting part and its corresponding recess are connected to one another pressure-tight by at least one insulating element, in particular an O-ring.

Besides improving the pressure-tightness, the O-rings cause a reduction of the streaming resistances in the area of the joints between handle and shaft, because the indentations or rises that occur are leveled by the O-rings.

According to a practical embodiment of the invention, the flushing and suction channels are configured as two separate channels in the handle. The handle advantageously has three separate channels, namely a light channel, a flushing channel, and a suction channel, so that the handle-side light channel in the shaft is continued in a separate light channel and the handle-side flushing and suction channels lead into the hollow shaft.

The exactly positioned joining of the handle, on the one hand, and the shaft, on the other, can be facilitated according to the invention centering aids are configured if on the handle and on the shaft. According to a preferred embodiment of the invention it is proposed that the centering aids take the form of pins mounted on the handle and/or on the shaft that can be inserted into corresponding recesses on the respective other component.

It is further proposed with the invention that the coupling mechanism is configured as a notching link. Notching links are distinguished in that, besides their simple construction, they ensure a good, sufficiently firm coupling of the components that are to be connected to one another and in addition can be activated in quick, simple manner.

To prevent accidental separation of shaft and handle, it is proposed with the invention that the notching connection can only be released again by means of the activation of a particular unlocking mechanism.

It is finally proposed with the invention that the unlocking mechanism is configured as a valve rocker mechanism that is actively connected with the notch connection.

Additional characteristics and advantages of the invention can be seen with reference to the accompanying illustration depicting in merely schematic form an embodiment of a medical instrument according to the invention for endoscopic interventions.

DETAILED DESCRIPTION OF THE INVENTION

Figure 1:
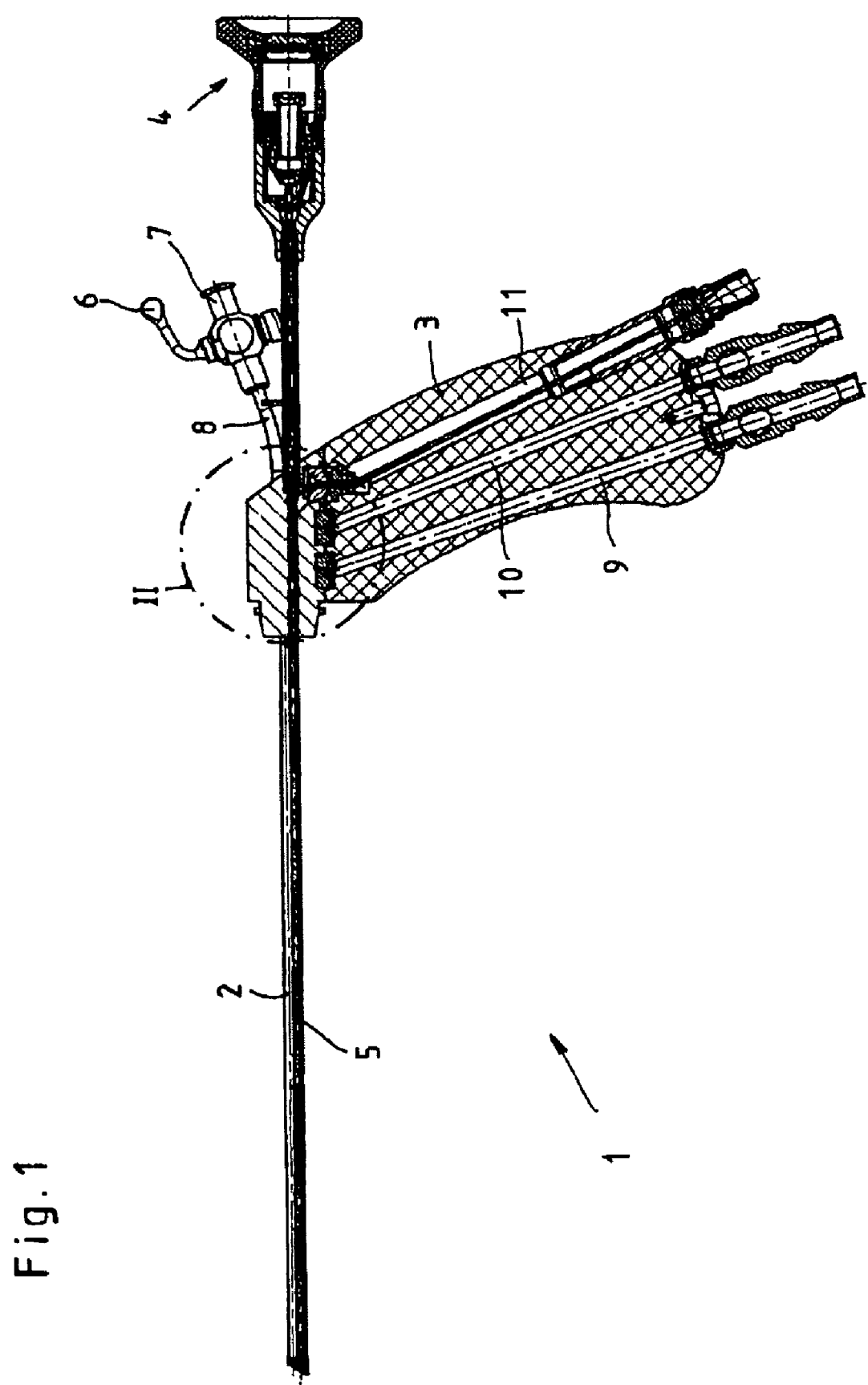
FIG. 1 shows a schematic side view of a medical instrument according to the invention for endoscopic interventions in a longitudinal section.

The illustration in FIG. 1 shows an endoscope 1, which consists essentially of a hollow shaft 2 and a handle 3 that supports the shaft 2. For examining the operating area and for guiding the instrument during an operation, the endoscope 1 has an optical system made up of various lenses and ending proximally in an eyepiece unit 4. To contain the lens systems that serve as image transmitters, an optical channel 5 is positioned in the hollow shaft 2 and leads proximally into the eyepiece unit 4.

On its proximal side the endoscope 1 in the illustrated cut-out side view has, in addition, an access 7 that can be locked by a valve 6 to a working channel 8 through which medical instruments such as cutting and/or gripping instruments can be introduced into the hollow shaft 2 and finally into the operating area. The valve 6 serves to lock the working channel 8 pressure-tight when there is no medical instrument inserted, in order to prevent dispersal of the gas serving to form the pneumo-peritoneum, for instance in laparoscopy.

Figure 3:
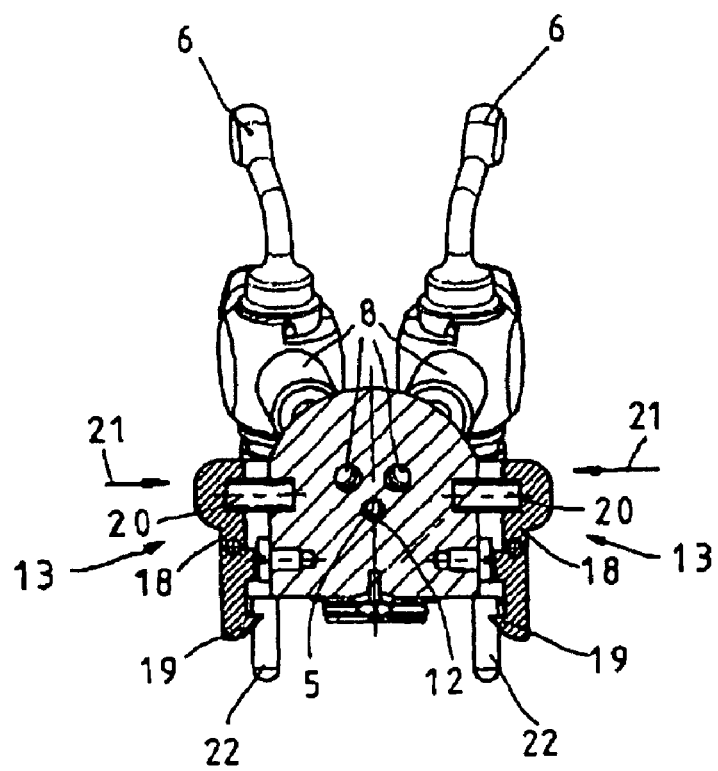
FIG. 3 shows a section along the line III-III of FIG. 2.

It is possible of course that the endoscope 1 has more than just one working channel 8 for inserting medical instruments, as can be seen for instance in the sectional drawing in FIG. 3.

Figure 2:
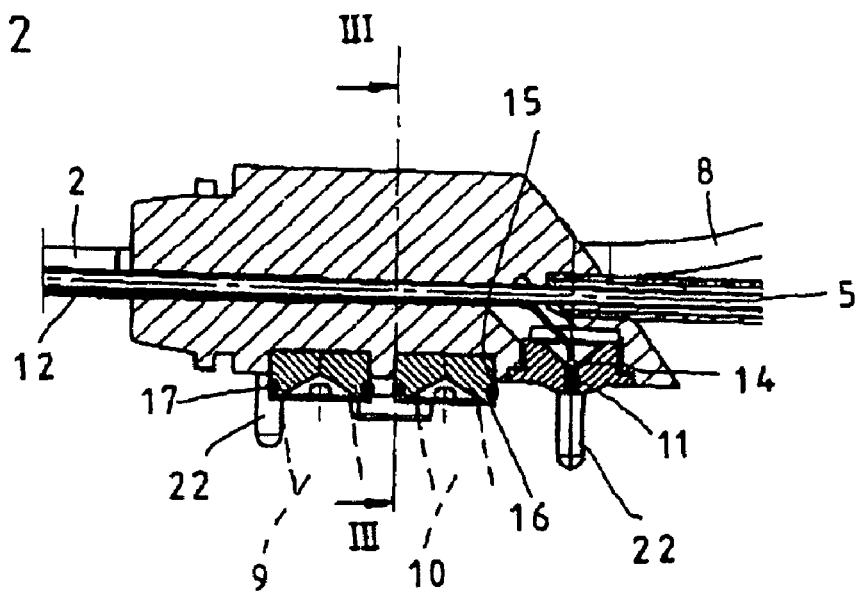
FIG. 2 shows an enlarged depiction of detail II of FIG. 1.

As can further be seen from FIGS. 1 and 2, in the handle 3 various channels, namely a suction channel 9, a flushing channel 10, and a light channel 11, are configured, which lead into the hollow shaft 2. Whereas the suction channel 9 and the flushing channel 10 merge freely into the hollow shaft 2, the handle-side light channel 11 continues in a light channel 12 in the shaft 2.

The handle 3 equipped with channels 9, 10, and 11 can be dissolubly secured on the shaft 2 by means of a coupling mechanism 13 depicted in FIG. 3.

The structure of the light channels 11 and 12, as well as of the coupling area between the handle 3 and the shaft 2, can be seen in particular from the enlarged detail view in FIG. 2.

Both the handle-side light channel 11 and the shaft-side light channel 12 are equipped with light-conducting fibers by which light proceeding from an external light source can be conducted to the operating area in order to permit observation of the operating area by means of the lens of the endoscope 1. To ensure minimal losses in transmission of light from the light-conducting fibers of the handle-side light channel 11 to the light-conducting fibers of the shaft-side light channel 12, the mutually facing end surfaces of the light-conducting fibers of the handle-side light channel 11 and of the shaft-side light channel 12 are ground and polished and, in addition, are aligned exactly centrally on one another. The central alignment of the light fiber clusters to one another prevents the formation of disturbing reflections.

To bridge an air gap 14 remaining between the mutually facing end surfaces of the light-conducting fibers of the handle-side light channel 11 and of the shaft-side light channel 12, and thus to minimize light losses occurring because of the air gap 14, an optically active substance such as an optical gel can be applied on the end surfaces of the light-conducting fibers.

As can be seen from FIG. 2, the light-conducting fiber cluster has a greater diameter in the handle-side light channel 11 than the light-conducting fiber cluster in the shaft-side light channel 12. Through the formation of the light-conducting clusters with various diameters, it is easily possible to compensate any centering errors in the coupling of the light channels 11 and 12. Advantageously, the light-conducting fiber cluster in the handle-side light channel 11 has the greater diameter, because first there is more space available in the handle 3 as in the instrument shaft 2 and second the light-source-side light conductor 11 is advantageously of greater diameter in order to ensure a complete illumination of the lens-side light conductor 12. It is of course also possible, however, to provide the light-conducting fiber cluster of the shaft-side light channel 12 with the greater diameter.

The handle 3 and the shaft 2 in the area of the suction channel 9 and of the flushing channel 10 are coupled by means of ring-shaped projecting parts 15 formed on the shaft 2, which in coupled position are inserted in corresponding circular-shaped recesses 16 on the handle, so that the circular-shaped recesses 16 coaxially surround the channels 9 and 10. In addition to the configuration of the transition of the channels 9 and 10 to the hollow shaft 2, the projecting parts 15 and recesses 16 serve to mutually center the shaft 2 and the handle 3 during coupling.

To ensure that the coupling spot on the shaft 2 and handle 3 in the area of the channels 9 and 10 are configured pressure tight, the ring-shaped projecting parts 15 are provided with insulating elements configured as O-rings 17. Alternatively to the illustrated structure of the projecting parts 15 and recesses 16, it is also possible of course to configure the projecting parts on the handle 3 and the recesses 16 for inserting the projecting parts 15 on the shaft 2. It is likewise possible to position the insulating elements, for instance the O-rings 17, in the recesses 16.

In addition to the improvement of pressurized firmness, the O-rings 17 cause a reduction of the streaming resistances in the areas of the joints between handle 3 and shaft 2, because indentations and rises occurring there are leveled by the O-rings 17.

Mutual securing of the shaft 2 and the handle 3 occurs in the illustrated embodiment by means of the coupling mechanism 13 shown in FIG. 3, which is configured as a notching connection. As can be seen in FIG. 3, the illustrated notching connection consists of two valve rockers 18 positioned on the shaft 2, on whose free ends facing the handle 3 there are notching pins 19, which in coupled position engage in corresponding notching recesses in the handle 3.

To prevent accidental release of the notching connection, the valve rockers 18 are configured in such a way that the notching can only be released again through active activation of both valve rockers 18. For this purpose, as can be seen in FIG. 3, the valve rockers 18 are configured in such a way that for each valve rocker 18 one spring element 20 is provided, which is in active connection with the respective valve rocker 18. As soon as pressure forces are exerted acting on the free ends of the valve rockers 18 in the direction of the arrow 21, the notching pins 19 are lifted out of the notching recesses on the handle 3, so that the shaft 2 can be removed from the handle 3.

Exactly positioned joining of the handle 3 on the one hand and the shaft 2 on the other, is facilitated in the illustrated embodiment through the fact that centering aids 22 are positioned as pins on the shaft 2 and are inserted into corresponding recesses in the handle 3. The length of the pins, which also can only be positioned on the handle 3 or on both components 2 and 3, is advantageously restricted so that the pins, which are inserted into the corresponding recesses in the other respective component, already secure the handle 3 and the shaft 2 relatively to one another before the components 2 and 3 are coupled to one another by means of the coupling mechanism 13.

A medical instrument of the described design for endoscopic interventions is distinguished in that the shaft 2 and the handle 3 are dissolubly connected to one another.

In addition to improved cleansing of both separate components 2 and 3, a medical instrument of this design is distinguished by a greater flexibility. Thus it is possible, for instance, to use one handle 3 for various shafts 2, or else to equip one shaft 2 with various handles 3 that, for instance, are adapted to particular individual demands or wishes of the operator. Without having to produce a complete instrument, it is thus possible to make available a medical instrument that can be employed in a considerable variety.

What is claimed is:

1. A medical instrument for endoscopic interventions having a hollow shaft for receiving at least one medical instrument and having a handle that supports the shaft, which handle contains at least one channel that continues in the hollow shaft, and which handle can be dissolubly secured on the shaft by means of a coupling mechanism, the at least one channel is configured as a flushing and/or suction channel, and, in the area of a coupling spot between the at least one handle-side channel and the hollow shaft, a projecting part and a corresponding recess for inserting the projecting part are configured on the shaft and on the handle, and configured between the at least one handle-side channel and the hollow shaft, there is at least one insulating element via which each projecting part and the respective corresponding recess are connected to each other in a pressure-tight manner, distinguished in that the coupling mechanism is configured as a notching connection with two spring-loaded valve rockers mounted on the shaft, and centering aids for joining the handle and the shaft together in an exact position are formed on the handle and/or on the shaft which centering aids are configured as pins that can be inserted into corresponding recesses on the other respective component to be coupled with, and the length of the pins is such that they already secure the shaft and the handle relatively to one another before shaft and handle are coupled to one another via the coupling mechanism.

2. A medical instrument according to claim 1, wherein the at least one channel is configured as a light channel provided with light-conducting fibers, distinguished in that a separate channel is positioned in the hollow shaft to receive the light-conducting fibers, and that the light-conducting fibers of a handle-side light channel and of a shaft-side light channel are ground and polished on their mutually facing end surfaces.

3. A medical instrument according to claim 2, distinguished in that in a coupled position the mutually facing end surfaces of the light-conducting fibers of the handle-side light channel and of the shaft-side light channel are aligned centrally on one another.

4. A medical instrument according to claim 2, distinguished in that in the area of a coupling spot between the handle-side light channel and the shaft-side light channel an optically active substance such as an optical gel can be applied on the ends of the light-conducting fibers.

5. A medical instrument according to claim 2, distinguished in that a light-conducting cluster in the handle-side or shaft-side light channel has a greater diameter than the light-conducting cluster in the respective shaft-side or handle-side light-conducting channel to be coupled with.

6. A medical instrument according to claim 1, distinguished in that in the handle two separate channels are configured that serve as flushing and suction channel.

7. A medical instrument according to claim 2, distinguished in that in the handle three channels are configured, namely a light channel, a flushing channel, and suction channel.

8. A medical instrument according to claim 1, distinguished in that the notching connection can be released by means of an unlocking mechanism.

9. A medical instrument according to claim 8, distinguished in that the un-locking mechanism is configured as a valve rocker mechanism that is in active connection with the notching connection.

10. A medical instrument according to claim 1, distinguished in that the at least one insulating element is configured as an O-ring.

* * * * *